(12) United States Patent
Hamada

(10) Patent No.: US 10,336,843 B2
(45) Date of Patent: Jul. 2, 2019

(54) ULTRA-HIGH MOLECULAR WEIGHT ETHYLENE-BASED COPOLYMER POWDER, AND MOLDED ARTICLE USING ULTRA-HIGH MOLECULAR WEIGHT ETHYLENE-BASED COPOLYMER POWDER

(71) Applicant: Asahi Kasei Kabushiki Kaisha, Tokyo (JP)

(72) Inventor: Yoshiaki Hamada, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/571,424

(22) PCT Filed: Mar. 6, 2017

(86) PCT No.: PCT/JP2017/008853
§ 371 (c)(1),
(2) Date: Nov. 2, 2017

(87) PCT Pub. No.: WO2017/163848
PCT Pub. Date: Sep. 28, 2017

(65) Prior Publication Data
US 2019/0002611 A1 Jan. 3, 2019

(30) Foreign Application Priority Data
Mar. 25, 2016 (JP) .................. 2016-061721

(51) Int. Cl.
| | |
|---|---|
| C08F 210/16 | (2006.01) |
| H01M 2/16 | (2006.01) |
| A61L 27/16 | (2006.01) |
| B29B 9/08 | (2006.01) |
| D01F 6/30 | (2006.01) |
| B29C 43/00 | (2006.01) |
| B29K 23/00 | (2006.01) |
| B29L 31/34 | (2006.01) |

(52) U.S. Cl.
CPC ............ *C08F 210/16* (2013.01); *A61L 27/16* (2013.01); *B29B 9/08* (2013.01); *B29C 43/003* (2013.01); *D01F 6/30* (2013.01); *H01M 2/1653* (2013.01); *A61L 2430/02* (2013.01); *B29K 2023/08* (2013.01); *B29L 2031/3468* (2013.01); *C08F 2800/10* (2013.01)

(58) Field of Classification Search
CPC . C08F 210/16; C08F 2800/10; H01M 2/1653; A61L 27/16; A61L 2430/02; B29B 9/08; B29C 43/003; D01F 6/30
See application file for complete search history.

(56) References Cited

U.S. PATENT DOCUMENTS

2004/0039115 A1    2/2004   Ishida
2008/0071031 A1    3/2008   Fujiawara et al.
2009/0324920 A1   12/2009   Takeyama et al.
2011/0165419 A1    7/2011   Kumamoto
2014/0221516 A1*   8/2014   Mikawa .................. C08L 23/20
                                                        521/134
2018/0194883 A1*   7/2018   Kim ....................... C08F 210/16

FOREIGN PATENT DOCUMENTS

| EP | 3098256 A1 | 11/2016 |
|---|---|---|
| JP | 2007-023171 A | 2/2007 |
| JP | 4173444 B2 | 8/2008 |
| JP | 2011-153171 A | 8/2011 |
| JP | 2012-229355 A | 11/2012 |
| JP | 2015-157905 A | 9/2015 |
| JP | 5876632 B1 | 3/2016 |
| WO | 2006/070886 A1 | 7/2006 |
| WO | 2008/001772 A1 | 6/2007 |
| WO | 2008/123526 A | 10/2008 |

OTHER PUBLICATIONS

International Search Report issued in corresponding International Patent Application No. PCT/JP2017/008853 dated Apr. 4, 2017.
Written Opinion issued in corresponding International Patent Application No. PCT/JP2017/008853 dated Apr. 4, 2017.
Supplementary European Search Report issued in corresponding European Patent Application No. 17769893.3 dated May 24, 2018.

* cited by examiner

*Primary Examiner* — Robert D. Harlan
(74) *Attorney, Agent, or Firm* — Morgan, Lewis & Bockius LLP

(57) ABSTRACT

An ultra-high molecular weight ethylene-based copolymer powder comprising:
an ethylene unit and an α-olefin unit having 3 or more and 8 or less carbon atoms as structural units,
wherein the ultra-high molecular weight ethylene-based copolymer powder has a viscosity-average molecular weight of 100,000 or more and 10,000,000 or less,
a content of the α-olefin unit is 0.01 mol % or more and 0.10 mol % or less based on a total amount of the ethylene unit and the α-olefin unit, and
in measurement with a differential scanning calorimeter under following conditions, an isothermal crystallization time is determined as a time from reaching 126° C. of Step A3 as a starting point (0 min) to giving an exothermic peak top due to crystallization and the isothermal crystallization time is 5 minutes or more. (Conditions for measurement of isothermal crystallization time)
Step A1: holding at 50° C. for 1 minute and then an increase up to 180° C. at a temperature rise rate of 10° C./min,
Step A2: holding at 180° C. for 30 minutes and then a decrease down to 126° C. at a temperature drop rate of 80° C./min, and
Step A3: holding at 126° C.

12 Claims, No Drawings

ULTRA-HIGH MOLECULAR WEIGHT ETHYLENE-BASED COPOLYMER POWDER, AND MOLDED ARTICLE USING ULTRA-HIGH MOLECULAR WEIGHT ETHYLENE-BASED COPOLYMER POWDER

TECHNICAL FIELD

The present invention relates to an ultra-high molecular weight ethylene-based copolymer powder and a molded article using the ultra-high molecular weight ethylene-based copolymer powder.

BACKGROUND ART

Since ultra-high molecular weight olefins, in particular, ultra-high molecular weight polyethylenes, have high molecular weights compared with general-purpose polyethylenes and thereby have excellent stretch processability, high strength, high chemical stability, and long period reliability, they have been used as starting materials of molded articles, such as microporous membranes for separators of secondary batteries represented by lead storage batteries and lithium ion batteries and fiber.

Ultra-high molecular weight olefins, in particular, ultra-high molecular weight polyethylenes, have various excellent characteristics, such as shock resistance, wear resistance, sliding property, low-temperature property, and chemical resistance, compared to general-purpose polyethylenes and have therefore been used in lining materials for, for example, hoppers and chutes; bearings; gears; roller guide rails; or molded articles, such as bone substitutes, bone conductive materials, and osteoinduction materials.

These ultra-high molecular weight polyethylenes have high molecular weights, and extrusion molding processing of such a resin alone is therefore difficult. Accordingly, in production of, for example, a microporous membrane for a secondary battery separator or fiber, an ultra-high molecular weight polyethylene powder is molded by kneading extrusion in many cases, for example, in an extruder in a state dissolved in a solvent under high temperature.

In addition, by the same reasons described above, molding by, for example, compression molding (press molding) and ram extrusion are also employed in many cases. It is important for both compression molded products and ram extruded products to achieve a balance between the shock resistance and the wear resistance. Examples of the method for achieving a balance between these characteristics are disclosed in Patent Literatures 1 to 3.

CITATION LIST

Patent Literature

Patent Literature 1: Japanese Patent Laid-Open No. 2007-23171
Patent Literature 2: Japanese Patent No. 4173444
Patent Literature 3: Japanese Patent Laid-Open No. 2015-157905

SUMMARY OF INVENTION

Technical Problem

However, in recent years, the technologies of Patent Literatures 1 and 2 are not sufficient from the viewpoint of wear resistance, the effects from the viewpoint of shock resistance are not mentioned, and it is desired to achieve a balance between higher wear resistance and shock resistance. Patent Literature 3 discloses a means for solving these problems.

At the same time, there is a technology of preparing a sheet (hereinafter, referred to as molded sheet) by molding an ultra-high molecular weight polyethylene by, for example, compression molding (press molding) or ram extrusion and cutting the resulting molded article to a skive shape. Such a case has a disadvantage of curving of the resulting molded sheet. In order to resolve this curving, aging may be performed, which results in problems of decreasing the productivity by an increase in the number of steps and also of being incapable of peeling the molded sheet from the mold used for aging.

In addition, contamination of the molded article with foreign substances is a common problem in separators for secondary batteries, fiber, compression molding (press molding), ram extrusion, etc. In particular, separators for secondary batteries and fiber may cause membrane breakage or thread breakage due to foreign substances, and these problems are needed to be solved.

The present invention has been made in view of the above-described problems, and it is an object of the invention to provide an ultra-high molecular weight ethylene-based copolymer powder that is not only capable of achieving a balance between wear resistance and shock resistance after molding but also capable of suppressing the curving of a molded sheet and allows the molded sheet to be easily peeled from the mold used for aging the sheet and also can suppress membrane breakage or thread breakage due to foreign substances in a separator for a secondary battery or fiber and to provide a molded article prepared using the ultra-high molecular weight ethylene-based copolymer powder.

Solution to Problem

Accordingly, the present inventors have diligently studied in order to achieve the above-mentioned objects and, as a result, have surprisingly found that use of an ultra-high molecular weight ethylene-based copolymer powder containing α-olefin within a specific amount range is not only capable of achieving a balance between shock resistance and wear resistance but also capable of suppressing the curving of a molded sheet and allows the molded sheet to be easily peeled from the mold used for aging the sheet and also can suppress membrane breakage or thread breakage due to foreign substances in a separator for a secondary battery or fiber, and have accomplished the present invention.

That is, the present invention is as follows:

[1] An ultra-high molecular weight ethylene-based copolymer powder comprising:
an ethylene unit and an α-olefin unit having 3 or more and 8 or less carbon atoms as structural units,
wherein the ultra-high molecular weight ethylene-based copolymer powder has a viscosity-average molecular weight of 100,000 or more and 10,000,000 or less,
a content of the α-olefin unit is 0.01 mol % or more and 0.10 mol % or less based on a total amount of the ethylene unit and the α-olefin unit, and
in measurement with a differential scanning calorimeter under following conditions, an isothermal crystallization time is determined as a time from reaching 126° C. of Step A3 as a starting point (0 min) to giving an exothermic peak top due to crystallization and the isothermal crystallization time is 5 minutes or more.

(Conditions for Measurement of Isothermal Crystallization Time)

Step A1: holding at 50° C. for 1 minute and then an increase up to 180° C. at a temperature rise rate of 10° C./min, Step A2: holding at 180° C. for 30 minutes and then a decrease down to 126° C. at a temperature drop rate of 80° C./min, and Step A3: holding at 126° C.

[2] The ultra-high molecular weight ethylene-based copolymer powder according to [1], wherein in measurement with a differential scanning calorimeter under following conditions, a heat of fusion per unit mass ($\Delta H2$) in a temperature rising process of Step B3 is 230 J/g or less.

(Conditions for Measuring Heat of Fusion Per Unit Mass ($\Delta H2$))

Step B1: holding at 50° C. for 1 minute and then an increase up to 180° C. at a temperature rise rate of 10° C./min, Step B2: holding at 180° C. for 5 minutes and then a decrease down to 50° C. at a temperature drop rate of 10° C./min, and Step B3: holding at 50° C. for 5 minutes and then an increase up to 180° C. at a temperature rise rate of 10° C./min.

[3] The ultra-high molecular weight ethylene-based copolymer powder according to [1] or [2], wherein a content of titanium element measured with an inductively coupled plasma mass spectrometer (ICP/MS) is 6 ppm or less.

[4] The ultra-high molecular weight ethylene-based copolymer powder according to any one of [1] to [3], wherein the isothermal crystallization time is 8 minutes or more.

[5] The ultra-high molecular weight ethylene-based copolymer powder according to any one of [1] to [4], wherein the ultra-high molecular weight ethylene-based copolymer powder has a tap density of 0.51 g/cm$^3$ or more and 0.64 g/cm$^3$ or less, and a bulk density of 0.40 g/cm$^3$ or more and 0.60 g/cm$^3$ or less;

[6] The ultra-high molecular weight ethylene-based copolymer powder according to [5], wherein a ratio of the tap density to the bulk density is 1.10 or more and 1.50 or less.

[7] The ultra-high molecular weight ethylene-based copolymer powder according to any one of [1] to [6], wherein the ultra-high molecular weight ethylene-based copolymer powder has an average particle diameter of 50 μm or more and 200 μm or less.

[8] A molded article of the ultra-high molecular weight ethylene-based copolymer powder according to any one of [1] to [7].

[9] The molded article according to [8], wherein the molded article is a separator membrane for a secondary battery or fiber prepared by wet extrusion;

[10] The molded article according to [9], wherein the secondary battery is a lithium ion secondary battery or a lead storage battery.

[11] The molded article according to [9], wherein a product using the fiber is rope, net, bulletproof clothing, a protective garment, protective gloves, a fiber reinforced concrete product, or a helmet.

[12] The molded article according to [8], wherein the molded article is used in a lining application, a bearing, a gear, a roller guide rail, a bone substitute, a bone conductive material, or an osteoinduction material.

Advantageous Effects of Invention

The present invention can realize an ultra-high molecular weight ethylene-based copolymer powder that is not only capable of achieving a balance between shock resistance and wear resistance of a molded product but also capable of suppressing the curving of a molded sheet and allows the molded sheet to be easily peeled from the mold used for aging the molded sheet and also can suppress membrane breakage or thread breakage due to foreign substances in a separator for a secondary battery or fiber, and to realize a molded article prepared using the ultra-high molecular weight ethylene-based copolymer powder.

DESCRIPTION OF EMBODIMENTS

Embodiments for implementing the present invention (hereinafter, referred to as "the Embodiment") will now be described in detail, but the present invention is not limited thereto and can be variously modified within a scope not departing from the gist of the invention.

[Ultra-High Molecular Weight Ethylene-Based Copolymer Powder]

The ultra-high molecular weight ethylene-based copolymer powder of the Embodiment comprises an ethylene unit and an α-olefin unit having 3 or more and 8 or less carbon atoms as structural units, wherein the ultra-high molecular weight ethylene-based copolymer powder has a viscosity-average molecular weight of 100,000 or more and 10,000,000 or less, a content of the α-olefin unit is 0.01 mol % or more and 0.10 mol % or less based on a total amount of the ethylene unit and the α-olefin unit, and in measurement with a differential scanning calorimeter under following conditions, an isothermal crystallization time is determined as a time from reaching 126° C. of Step A3 as a starting point (0 min) to giving an exothermic peak top due to crystallization and the isothermal crystallization time is 5 minutes or more.

(Conditions for Measurement of Isothermal Crystallization Time)

Step A1: holding at 50° C. for 1 minute and then an increase up to 180° C. at a temperature rise rate of 10° C./min, Step A2: holding at 180° C. for 30 minutes and then a decrease down to 126° C. at a temperature drop rate of 80° C./min, and Step A3: holding at 126° C.

Throughout the specification, each monomer unit constituting a polymer is named according to nomenclature for the monomer from which the monomer unit is derived. For example, the term "ethylene unit" refers to a structural unit of a polymer generated by polymerization of ethylene as a monomer, and the structure has a polymer main chain of the two carbon atoms of ethylene in the molecular structure. Similarly, the term "α-olefin unit" refers to a structural unit of a polymer generated by polymerization of α-olefin as a monomer, and the structure has a polymer main chain of the two carbon atoms of olefin derived from α-olefin in the molecular structure.

The ultra-high molecular weight ethylene-based copolymer powder may be any ethylene copolymer that comprises an ethylene unit and an α-olefin unit having 3 or more and 8 or less carbon atoms. The α-olefin having 3 or more and 8 or less carbon atoms that is copolymerizable with ethylene is not particularly limited and is specifically at least one α-olefin selected from the group consisting of linear, branched, or cyclic α-olefins; compounds represented by a formula: $CH_2=CHR^1$ (where, $R^1$ denotes an aryl group having 1 to 6 carbon atoms); and linear, branched, or cyclic dienes having 4 to 7 carbon atoms. Among these α-olefins, propylene and 1-butene are preferred from the viewpoint of wear resistance, heat resistance, and strength of molded articles.

[Viscosity-Average Molecular Weight]

The viscosity-average molecular weight (Mv) is 100,000 or more and 10,000,000 or less, more preferably 150,000 or more and 9,500,000 or less, and most preferably 200,000 or more and 9,000,000 or less. An Mv of 100,000 or more further improves the wear resistance and the strength. In addition, an Mv of 10,000,000 or less further improves the moldability. Furthermore, an Mv within the above-mentioned range provides high productivity of powder. The ultra-high molecular weight ethylene-based copolymer powder having these characteristics can be suitably used in, for example, molding of a separator for a secondary battery or molding of fiber by compression molding (press molding), ram extrusion, or extrusion kneading in a state dissolved in a solvent. The resulting molded article can be suitably used in a wide range of applications.

As a method of controlling the Mv within the above-mentioned range, for example, the polymerization temperature of the reactor used in the polymerization of the ultra-high molecular weight ethylene-based copolymer powder is changed. In general, the Mv tends to decrease with an increase in the polymerization temperature, and the Mv tends to increase with a decrease in the polymerization temperature. As another method of controlling the Mv within the above-mentioned range, for example, the type of the organometallic compound to be added as a promoter in the polymerization of the ultra-high molecular weight ethylene-based copolymer powder is changed. Alternatively, a chain transfer agent may be added during the polymerization of an ultra-high molecular weight polyethylene copolymer. Such addition of a chain transfer agent tends to decrease the Mv of the ultra-high molecular weight ethylene-based copolymer powder regardless of the polymerization temperature.

The Mv of an ultra-high molecular weight ethylene-based copolymer powder can be calculated by the following Mathematical Expression A from the limiting viscosity [η] (dL/g) determined by dissolving the ultra-high molecular weight ethylene-based copolymer powder in a decahydronaphthalene solution at different concentrations and extrapolating the reduced viscosity determined at 135° C. to zero concentration. More specifically, the Mv can be determined by the method described in Examples.

$$Mv=(5.34\times10^{-4})\times[\eta]^{1.49}$$  Mathematical Expression A.

[Content of Ethylene Unit]

The content of the ethylene unit is 99.90 mol % or more and 99.99 mol % or less, more preferably 99.905 mol % or more and 99.99 mol % or less, and most preferably 99.91 mol % or more and 99.99 mol % or less based on the total amount of the ethylene unit and the α-olefin unit. The content of the ethylene unit within the above-mentioned range tends to further enhance the heat resistance and/or the strength.

[Content of α-olefin Unit]

The content of the α-olefin unit is 0.01 mol % or more and 0.10 mol % or less, preferably 0.01 mol % or more and 0.095 mol % or less, and more preferably 0.01 mol % or more and 0.09 mol % or less based on the total amount of the ethylene unit and the α-olefin unit. The content of the α-olefin unit within the above-mentioned range tends to further improve the shock resistance and the wear resistance. The content of the α-olefin unit is measured in accordance with the method disclosed in G. J. Ray, et al., Macromolecules, 10, 773 (1977). The content of the α-olefin unit can be calculated from the integrated intensity using the methylene carbon signal observed in the $^{13}$C-NMR spectrum. More specifically, the content can be measured by the method described in Examples.

[Isothermal Crystallization Time]

In the Embodiment, the isothermal crystallization time is the time at an exothermic peak top due to crystallization at 126° C., and in the measurement with a differential scanning calorimeter (DSC) under the following measurement conditions, the time from reaching 126° C. of Step A3 as a starting point (0 min) to giving an exothermic peak top due to crystallization is defined as the isothermal crystallization time.

Step A1: holding at 50° C. for 1 minute and then an increase up to 180° C. at a temperature rise rate of 10° C./min, Step A2: holding at 180° C. for 30 minutes and then a decrease down to 126° C. at a temperature drop rate of 80° C./min, and Step A3: holding at 126° C.

The isothermal crystallization time must be 5 minutes or more and is preferably 7 minutes or more and more preferably 8 minutes or more. A molded sheet obtained by cutting a molded article prepared by, for example, compression molding (press molding) or ram extrusion to a skive shape may be curved. In order to resolve this curving, the molded sheet may be sandwiched between molds for aging. If the isothermal crystallization time is less than 5 minutes, not only the molded sheet is readily curved, but also after aging of the curved molded sheet, the sheet cannot be peeled from the molds used for the aging.

As a method of controlling the isothermal crystallization time within the above-mentioned range, it is conceivable that the catalyst is kept from being localized in the polymerization reactor. Specifically, for example, the catalyst concentration for the inert hydrocarbon medium is controlled to 10 g/L or less; the catalyst and the inert hydrocarbon medium are supplied to a polymerization reactor from a plurality of catalyst feeding openings; four or more stirring blades are used in a stirring device; and the rotation speed of the stirring blades is controlled to 60 rpm or more.

[Heat of Fusion Per Unit Mass (ΔH2)]

In the measurement with a differential scanning calorimeter under following conditions, a heat of fusion per unit mass in a temperature rising process of Step B3 (the heat of fusion per unit mass in the second temperature rising process) is defined as the heat of fusion per unit mass (ΔH2). (Conditions for Measuring Heat of Fusion Per Unit Mass (ΔH2))

Step B1: holding at 50° C. for 1 minute and then an increase up to 180° C. at a temperature rise rate of 10° C./min, Step B2: holding at 180° C. for 5 minutes and then a decrease down to 50° C. at a temperature drop rate of 10° C./min, and Step B3: holding at 50° C. for 5 minutes and then an increase up to 180° C. at a temperature rise rate of 10° C./min.

On this occasion, the heat of fusion per unit mass (ΔH2) is preferably 230 J/g or less, more preferably 50 J/g or more and 220 J/g or less, and most preferably 100 J/g or more and 210 J/g or less. A heat of fusion per unit mass (ΔH2) of 50 J/g or more can maintain the strength as a molded article, and a heat of fusion per unit mass (ΔH2) of 230 J/g or less tends to further suppress the curving of a molded sheet obtained by cutting a molded article prepared by, for example, compression molding (press molding) or ram extrusion to a skive shape. In addition, it is possible to omit the aging for resolving the curving of a molded sheet by sandwiching the molded sheet between molds, and therefore the operation of peeling the molded sheet from the molds is not necessary. Accordingly, the problem of incapable of peeling a molded sheet from molds can be avoided.

As a method of controlling the heat of fusion per unit mass ($\Delta H2$) within the above-mentioned range, it is conceivable that the catalyst is kept from being localized in the polymerization reactor. Specifically, for example, the catalyst concentration for the inert hydrocarbon medium is controlled to 10 g/L or less; the catalyst and the inert hydrocarbon medium are supplied to a polymerization reactor from a plurality of catalyst feeding openings; four or more stirring blades are used in a stirring device; and the rotation speed of the stirring blades is controlled to 60 rpm or more.

[Content of Titanium Element]

The content of titanium element defined by that measured with an inductively coupled plasma mass spectrometer (ICP/MS). The content of titanium element is preferably 6 ppm or less, more preferably 0.1 ppm or more and 5.5 ppm or less, and most preferably 0.5 ppm or more and 5 ppm or less. The content of titanium element is preferably 0.1 ppm or more from the viewpoint of acid resistance. A content of 6 ppm or less tends to further suppress the isothermal crystallization time from being shortened to less than 5 minutes and the heat of fusion per unit mass ($\Delta H2$) from increasing to over 150 J/g. Consequently, contamination of the molded article with foreign substances can be suppressed. In particular, in a separator for a secondary battery or fiber, an effect of reducing occurrence of membrane breakage or thread breakage due to foreign substances is exhibited. The content of titanium element contained in the ultra-high molecular weight ethylene-based copolymer powder can be controlled by the productivity of the ultra-high molecular weight ethylene-based copolymer powder per unit catalyst. The content can be decreased by increasing the productivity. The titanium content can be measured by the method described in Examples.

[Tap Density and Bulk Density]

The ultra-high molecular weight ethylene-based copolymer powder preferably has a tap density of 0.51 g/cm$^3$ or more and 0.64 g/cm$^3$ or less, more preferably 0.52 g/cm$^3$ or more and 0.63 g/cm$^3$ or less, and most preferably 0.53 g/cm$^3$ or more and 0.62 g/cm$^3$ or less. The ultra-high molecular weight ethylene-based copolymer powder having a tap density within the above-mentioned range is sufficiently loaded during the molding, and a uniform molded article can therefore be obtained. Consequently, there is a tendency of suppressing the curving of the molded sheet when the molded article is cut to a skive shape.

The ultra-high molecular weight ethylene-based copolymer powder preferably has a bulk density of 0.40 g/cm$^3$ or more and 0.60 g/cm$^3$ or less, more preferably 0.40 g/cm$^3$ or more and 0.58 g/cm$^3$ or less, and most preferably 0.40 g/cm$^3$ or more and 0.55 g/cm$^3$ or less. The ultra-high molecular weight ethylene-based copolymer powder having a bulk density of 0.40 g/cm$^3$ or more tends to have sufficiently high fluidity and excellent handling properties, to be stably fed to various molding devices, and to stabilize the dimensions of the molded product. In contrast, the ultra-high molecular weight ethylene-based copolymer powder having a bulk density of 0.60 g/cm$^3$ or less tends to exhibit, for example, high productivity in processing of molded products and to show better processing applicability.

The ratio of the tap density to the bulk density is preferably 1.10 or more and 1.50 or less, more preferably 1.10 or more and 1.48 or less, and most preferably 1.10 or more and 1.45 or less. A ratio of the tap density to the bulk density within the above-mentioned range tends to be more excellent in a balance of suppression of curving of molded sheets, processing applicability, and dimensional stability of molded articles.

In general, the bulk density can be controlled by the productivity of the ultra-high molecular weight ethylene-based copolymer powder per unit catalyst, although it varies depending on the catalyst to be used. The bulk density of the ultra-high molecular weight ethylene-based copolymer powder can be controlled by the polymerization temperature during the polymerization of the ultra-high molecular weight ethylene-based copolymer powder. The bulk density can be decreased by increasing the polymerization temperature. In addition, the bulk density of the ultra-high molecular weight ethylene-based copolymer powder can also be controlled by the slurry concentration in a polymerization vessel. The bulk density can be increased by increasing the slurry concentration. The bulk density of an ultra-high molecular weight ethylene-based copolymer powder can be measured by the method described in Examples.

In order to control the tap density within the above-mentioned range, it is important that the ultra-high molecular weight ethylene-based copolymer powder does not aggregate. As a means of preventing the aggregation, for example, the catalyst is kept from being localized in the polymerization reactor. Specifically, for example, the catalyst concentration to the inert hydrocarbon medium is controlled to 10 g/L or less; the catalyst and the inert hydrocarbon medium are supplied to a polymerization reactor from a plurality of catalyst feeding openings; four or more stirring blades are used in a stirring device; and the rotation speed of the stirring blades is controlled to 60 rpm or more. In addition, it is effective to suppress electrostatic adhesion of the polymer to the polymerization reactor. Specifically, as disclosed in the paragraph [0081] of Patent Literature 3, the amount of Stadis 450 to be added is preferably 20 ppm or more and 50 ppm or less.

The ratio of the tap density to the bulk density can also be controlled by the above-described method. Furthermore, blending of a lubricant, such as calcium stearate described below, is also a preferred method.

[Average Particle Diameter]

The ultra-high molecular weight ethylene-based copolymer powder preferably has an average particle diameter of 50 μm or more and 200 μm or less, more preferably 60 μm or more and 190 μm or less, and most preferably 70 μm or more and 180 μm or less. The ultra-high molecular weight ethylene-based copolymer powder having an average particle diameter of 50 μm or more tends to have better handling properties, such as charging of a hopper with the ultra-high molecular weight ethylene-based copolymer powder and weighing of the powder from the hopper. In contrast, if the average particle diameter is 200 μm or less, the processing applicability, such as productivity, tends to be more excellent in various molding processing steps. The average particle diameter of the ultra-high molecular weight ethylene-based copolymer powder can be controlled by the particle diameter of the catalyst to be used and also can be controlled by the productivity of the ultra-high molecular weight ethylene-based copolymer powder per unit catalyst. The average particle diameter of an ultra-high molecular weight ethylene-based copolymer powder can be measured by the method described in Examples described below.

The ultra-high molecular weight ethylene-based copolymer powder may be directly molded and processed with various molding devices or may be, after being mixed with an organic peroxide, molded and processed with various molding and processing devices. The case of molding and processing with various molding devices after mixing with an organic peroxide has a problem of occurrence of uneven crosslinking. However, in the ultra-high molecular weight ethylene-based copolymer powder of the Embodiment, a crosslinking reaction preferentially proceeds at the tertiary carbon derived from a slight amount of α-olefin present in the molecular chain, and a uniform crosslinking reaction proceeds. Consequently, the wear resistance of the molded product is further improved.

The organic peroxide (organic peroxide crosslinking agent) used in molding of the ultra-high molecular weight ethylene-based copolymer powder may be any organic material that contributes to crosslinking of the ultra-high molecular weight ethylene-based copolymer powder and has an atomic group —O—O— in the molecule, and examples thereof include organic peroxides, such as dialkyl peroxides, diacyl peroxides, hydroperoxide, and ketone peroxides; organic peresters, such as alkyl peresters; and peroxydicarbonates. Examples of the organic peroxide include, but not limited to, dicumyl peroxide, di-tert-butyl peroxide, 2,5-dimethyl-2,5-di-(tert-butylperoxy)hexane, 2,5-dimethyl-2,5-di-(tert-butylperoxy)hexyne-3,1,3-bis(tert-butylperoxyisopropyl)benzene, 1,1-bis(tert-butylperoxy)-3,3,5-trimethylcyclohexane, n-butyl-4,4-bis(tert-butylperoxy)valerate, benzoyl peroxide, p-chlorobenzoyl peroxide, 2,4-dichlorobenzoyl peroxide, tert-butyl peroxybenzoate, tert-butyl perbenzoate, tert-butylperoxyisopropyl carbonate, diacetyl peroxide, lauroyl peroxide, tert-butylcumyl peroxide, and α,α'-di(tert-butylperoxy)diisopropyl benzene. Among these organic peroxides, preferred are 2,5-dimethyl-2,5-bis(t-butylperoxy)hexane (trade name: "Perhexa 25B", manufactured by NOF Corporation), 2,5-dimethyl-2,5-bis(t-butyloxy)hexyne-3 (trade name: "Perhexyne 25B", manufactured by NOF Corporation), dicumyl peroxide, and 1,1-bis(t-butylperoxy)-3,3,5-trimethylcyclohexane.

The ultra-high molecular weight ethylene-based copolymer powder and the organic peroxide can be mixed using an ordinary mixer. For example, mixing with a stirrer, such as a Henschel mixer, or mixing by rotation, for example, in a blender is preferred. The stirring and mixing conditions in such a case vary depending on the conditions, such as temperature, pressure, and stirring rate, and cannot be unconditionally determined. However, for example, under normal temperature and normal pressure, stirring and mixing may be performed at a speed of 50 to 800 rotations per minute for about 1 to 10 minutes. The stirring and mixing speed may be appropriately changed. For example, mixing is first performed at a low speed for several minutes to mix the blending components uniformly to some extent, and stirring and mixing may be then performed at a higher speed for several minutes. The organic peroxide to be mixed with the ultra-high molecular weight ethylene-based copolymer powder may be directly used or may be added after being dissolved in, for example, a hydrocarbon solvent.

[Method of Molding Ultra-High Molecular Weight Ethylene-Based Copolymer Powder]

Examples of the method of molding the ultra-high molecular weight polyethylene, which is difficult to be molded by a method of molding common polyethylene, include compression molding (press molding) and extrusion molding. In the compression molding, a starting material powder is uniformly sprayed in a mold and is heated and pressed for molding, and the molded product is then cooled and taken out. A plate-like molded article can be directly used as a product and can be finished to a final product by, for example, being made into a block and performing machining. In the extrusion molding, molding of a separator for a secondary battery by extrusion kneading or fiber molding are performed, in an extruder, in a state dissolved in a solvent under high temperature, or a ram extruder, which performs extrusion by moving a piston back and forth, is used. Molded articles having a variety of shapes, such as a sheet, plate, irregular shape, and pipe, can be obtained by modifying the shape of the outlet of the extruder.

[Method of Producing Ultra-High Molecular Weight Ethylene-Based Copolymer Powder]

The ultra-high molecular weight ethylene-based copolymer powder can be produced using a general Ziegler-Natta catalyst or metallocene catalyst without any limitation. In particular, production using a Ziegler-Natta catalyst is preferred. The Ziegler-Natta catalyst is disclosed in paragraphs [0032] to [0068] of Patent Literature 3.

When a solid catalyst component and an organometallic compound component (hereinafter, abbreviated as "catalyst") are added to a polymerization system under ethylene polymerization conditions, both catalysts may be separately added to the polymerization system or may be mixed in advance and then added to the polymerization system. The both may be combined at any ratio, and the amount of the organometallic compound component is preferably 0.01 mmol or more and 1,000 mmol or less, more preferably 0.1 mmol or more and 500 mmol or less, and most preferably 1 mmol or more and 100 mmol or less based on 1 g of the solid catalyst component. Another purpose of mixing of the both is, for example, prevention of electrostatic adhesion to a storage tank, pipe, etc.

Examples of the polymerization in the method of producing the ultra-high molecular weight ethylene-based copolymer powder include suspension polymerization for (co)polymerizing a monomer containing ethylene or α-olefin having 3 or more and 8 or less carbon atoms. Polymerization by the suspension polymerization is preferable in that the heat of polymerization can be efficiently removed. In the suspension polymerization, an inert hydrocarbon medium can be used as a medium. The olefin itself also can be used as a medium.

The inert hydrocarbon medium is not particularly limited, and examples thereof include aliphatic hydrocarbons, such as propane, butane, isobutane, pentane, isopentane, hexane, heptane, octane, decane, dodecane, and kerosene; alicyclic hydrocarbons, such as cyclopentane, cyclohexane, and methylcyclopentane; aromatic hydrocarbons, such as benzene, toluene, and xylene; halogenated hydrocarbons, such as ethyl chloride, chlorobenzene, and dichloromethane; and mixtures thereof.

As described above, in implementing the present invention, it is important to prevent the catalyst from localizing in the polymerization reactor. Examples of the method thereof include that the catalyst concentration to the inert hydrocarbon medium is controlled to 10 g/L or less; the catalyst and the inert hydrocarbon medium are supplied to a polymerization reactor from a plurality of catalyst feeding openings; four or more stirring blades are used in a stirring device; and the rotation speed of the stirring blades is controlled to 60 rpm or more.

Generally, the polymerization temperature in the method of preparing an ultra-high molecular weight ethylene-based copolymer powder within the above-mentioned ranges is preferably 20° C. or more and 100° C. or less, more preferably 30° C. or more and 95° C. or less, and most preferably 40° C. or more and 90° C. or less. A polymerization temperature of 20° C. or more allows efficient industrial production. In contrast, a polymerization temperature of 100° C. or less allows continuous safe operation.

Generally, the polymerization pressure in the method of preparing an ultra-high molecular weight ethylene-based copolymer powder within the above-mentioned ranges is preferably normal pressure or more and 2 MPa or less, more preferably 0.1 MPa or more and 1.5 MPa or less, and most preferably 0.2 MPa or more and 1.0 MPa or less. A polymerization pressure of normal pressure or more tends to give an ultra-high molecular weight ethylene-based copolymer powder with a high total amount of metals and a high total amount of chlorine, whereas a polymerization pressure of 2 MPa or less tends to allow stable production of an ultra-high molecular weight ethylene-based copolymer powder with a low total amount of metals and a low total amount of chlorine.

The polymerization can be also carried out in two or more stages of different reaction conditions. Furthermore, for example, as described in the specification of West German Patent Publication No. 3127133, the molecular weight of an ultra-high molecular weight ethylene-based copolymer powder can also be adjusted by adding hydrogen to the polymerization system or changing the polymerization temperature. The molecular weight can be controlled within an appropriate range by adding hydrogen as a chain transfer agent to the polymerization system. In addition of hydrogen to the polymerization system, the mole fraction of hydrogen is preferably 0.01 mol % or more and 10 mol % or less, more preferably 0.01 mol % or more and 5 mol % or less, and most preferably 0.01 mol % or more and 1 mol % or less. In the Embodiment, the polymerization system can contain other known components that are useful for the production of an ultra-high molecular weight ethylene-based copolymer powder, in addition to the components described above.

In general, in polymerization of the ultra-high molecular weight ethylene-based copolymer powder, in order to suppress the electrostatic adhesion of the polymer to the polymerization reactor, an antistatic agent, such as Stadis 450 manufactured by The Associated Octel Company (distributor: Maruwa Bussan K. K.), can also be used. Stadis 450 can also be added to a polymerization reactor in a state diluted with an inert hydrocarbon medium using a pump etc. In such a case, the amount to be added is preferably 0.1 ppm or more and 50 ppm or less and more preferably 10 ppm or more and 30 ppm or less based on the amount of the ultra-high molecular weight ethylene-based copolymer powder produced per unit time.

The drying method after polymerization for preparing an ultra-high molecular weight ethylene-based copolymer powder within the above-described ranges is preferably a drying method of applying heat as little as possible. The dryer type is preferably, for example, a rotary kiln system, a puddle system, or a fluidized bed dryer. The drying temperature is preferably 50° C. or more and 150° C. or less and more preferably 70° C. or more and 100° C. or less. In addition, it is effective to enhance the drying by introducing an inert gas, such as nitrogen, to the dryer.

[Other Components]

The ultra-high molecular weight ethylene-based copolymer powder as described above may be used in combination with various known additives as needed. Any thermal stabilizer can be used, and examples thereof include heat stabilizers, such as tetrakis[methylene(3,5-di-t-butyl-4-hydroxy)hydrocinnamate]methane and distearylthiodipropionate; and weathering stabilizers, such as bis(2,2',6,6'-tetramethyl-4-piperidine)sebacate and 2-(2-hydroxy-t-butyl-5-methylphenyl)-5-chlorobenzotriazole. In addition, stearates, such as calcium stearate, magnesium stearate, and zinc stearate, which are known as a lubricant or a hydrogen chloride absorber, are also suitable additives.

[Molded Article]

The molded article of the Embodiment is a molded article using the above-described ultra-high molecular weight ethylene-based copolymer powder. The molded article contains the ultra-high molecular weight ethylene-based copolymer powder and may further contain an organic peroxide as needed. Such a molded article has high wear resistance and strength, excellent product physical properties, and excellent long-term stability, while maintaining other various physical properties.

[Use]

The ultra-high molecular weight ethylene-based copolymer powder prepared as described above can have advanced processability and high continuous process productivity and can be processed by a variety of processing methods. The molded article using the ultra-high molecular weight ethylene-based copolymer powder can be applied to a variety of uses. As principal uses, the molded article can be suitably used in, for example, separators for secondary batteries, such as a lithium ion secondary battery and a lead storage battery; fiber; lining materials for, for example, hoppers and chutes, having non-tackiness and low coefficients of friction; and bearings, gears, roller guide rails, bone substitutes, bone conductive materials, and osteoinduction materials, which are required to be self-lubricating, have a low coefficient of friction, and be wear resistant.

EXAMPLES

The present invention will now be described in more detail by Examples and Comparative Examples, but is not limited by the following Examples.

[Measurement Method and Conditions]

(1) Viscosity-Average Molecular Weight (Mv)

The viscosity-average molecular weight of an ultra-high molecular weight ethylene-based copolymer powder was determined by the following method in accordance with ISO 1628-3 (2010). First, 20 mg of the ultra-high molecular weight ethylene-based copolymer powder was weighed in a melting tube. The melting tube was nitrogen purged, and 20 mL of decahydronaphthalene (containing 1 g/L of 2,6-di-t-butyl-4-methylphenol) was then added to the tube, followed by stirring at 150° C. for 2 hours to dissolve the ultra-high molecular weight ethylene-based copolymer powder. The solution was subjected to measurement of falling time (ts) between marked lines in a thermostat of 135° C. with a Cannon-Fenske viscometer (manufactured by Sibata Scientific Technology Ltd., Product No. 100). Similarly, the falling time (ts) between marked lines was measured for each sample similarly prepared except that the amount of the ultra-high molecular weight ethylene-based copolymer powder was changed to 10 mg, 5 mg, and 2.5 mg. The falling time (tb) of decahydronaphthalene as a blank sample not containing the ultra-high molecular weight ethylene-based copolymer powder was measured. The reduced viscosities ($\eta_{sp}/C$) of the ultra-high molecular weight ethylene-based copolymer powder determined in accordance with the following expression were plotted to derive a linear expression between the concentration (C) (unit: g/dL) and the reduced viscosity ($\eta_{sp}/C$) of the ultra-high molecular weight ethylene-based copolymer powder, and the limiting viscosity ([η]) extrapolated to zero concentration was determined.

$$\eta_{sp}/C = (ts/tb - 1)/0.1 \text{(unit: dL/g)}.$$

Next, the viscosity-average molecular weight (Mv) was calculated using the following mathematical expression A and the value of the limiting viscosity [η].

$$Mv = (5.34 \times 10^4) \times [\eta]^{1.49} \qquad \text{Mathematical Expression A.}$$

(2) Content of α-olefin Unit

The content (mol %) of polymerization unit derived from α-olefin in the ultra-high molecular weight ethylene-based copolymer powder was measured in accordance with the method disclosed in G. J. Ray, et al., Macromolecules, 10, 773 (1977) and was calculated from the integrated intensity using the methylene carbon signal observed in the $^{13}$C-NMR spectrum.

Measuring device: ECS-400, manufactured by JEOL Ltd.
Observation nucleus: $^{13}$C
Observation frequency: 100.53 MHz
Pulse width: 45° (7.5 μsec)
Pulse program: single pulse dec
PD: 5 sec
Measurement temperature: 130° C.
Cumulative number: 30,000 times or more
Standard: PE (-eee-) signal, 29.9 ppm
Solvent: o-dichlorobenzene-d4
Sample concentration: 5 to 10 wt %
Melting temperature: 130° C. to 140° C.

(3) Isothermal Crystallization Time

The isothermal crystallization time was measured with DSC (manufactured by PerkinElmer, trade name: DSC 8000). An aluminum pan was charged with 8 to 10 mg of the ultra-high molecular weight ethylene-based copolymer powder and was set to the DSC. The time at which an exothermic peak top due to the crystallization at 126° C. was then measured under the following measurement conditions, and the measured time was defined as the isothermal crystallization time.

Step A1: holding at 50° C. for 1 minute and then an increase up to 180° C. at a temperature rise rate of 10° C./min,
Step A2: holding at 180° C. for 30 minutes and then a decrease down to 126° C. at a temperature drop rate of 80° C./min, and
Step A3: holding at 126° C.

(4) Heat of Fusion Per Unit Mass (ΔH2)

The heat of fusion per unit mass (ΔH2) was measured with DSC (manufactured by PerkinElmer, trade name: DSC 8000). An aluminum pan was charged with 8 to 10 mg of the ultra-high molecular weight ethylene-based copolymer powder and was set to the DSC. The heat of fusion per unit mass (ΔH2) in the temperature rising process of Step B3 was then measured under the following measurement conditions.

Step B1: holding at 50° C. for 1 minute and then an increase up to 180° C. at a temperature rise rate of 10° C./min,
Step B2: holding at 180° C. for 5 minutes and then a decrease down to 50° C. at a temperature drop rate of 10° C./min, and
Step B3: holding at 50° C. for 5 minutes and then an increase up to 180° C. at a temperature rise rate of 10° C./min.

(5) Content of Titanium Element

The ultra-high molecular weight ethylene-based copolymer powder was pressure-decomposed with a microwave decomposition apparatus (Model ETHOS TC, manufactured by Milestone General K. K.), and the element concentration of titanium as a metal in the ultra-high molecular weight ethylene-based copolymer powder was measured with an inductively coupled plasma mass spectrometer (ICP-MS, Model X series X7, manufactured by Thermo Fisher Scientific Inc.) by an internal standard method.

(6) Bulk Density

The bulk density of the ultra-high molecular weight ethylene-based copolymer powder was measured in accordance with JIS K-6721: 1997.

(7) Tap Density

The tap density of the ultra-high molecular weight ethylene-based copolymer powder was measured by the method described in JIS K-7370: 2000. The ratio of the tap density to the bulk density was calculated from the measurement results in (6) and (7).

(8) Average Particle Diameter

The average particle diameter of the ultra-high molecular weight ethylene-based copolymer powder was determined as the particle diameter at 50% of the weight in an integral curve obtained by classifying 100 g of the ultra-high molecular weight ethylene-based copolymer powder using 10 types of sieves (mesh size: 710 μm, 500 μm, 425 μm, 355 μm, 300 μm, 212 μm, 150 μm, 106 μm, 75 μm, and 53 μm) prescribed in JIS 28801 and integrating the weight of the particles remained on each sieve from the side of larger mesh size.

(9) Molding Method (9-1) Molding of Microporous Membrane

A polymer mixture was prepared by charging a 100 cc cup with 4.0 g of an ultra-high molecular weight ethylene-based copolymer powder and 0.012 g (0.3 mass %) of pentaerythritol-tetrakis[3-(3,5-di-t-butyl-4-hydroxyphenyl)propionate] as an oxidation inhibitor and performing dry blending. Furthermore, 36.0 g (polyethylene concentration: 10 mass %) of liquid paraffin (kinematic viscosity at 37.78° C.: $7.59 \times 10^{-5}$ m$^2$/s) was added to the mixture, followed by stirring with a spatula at room temperature to obtain a uniform slurry.

The slurry was charged into a Labo Plastmill (manufactured by Toyo Seiki Seisaku-sho, Ltd., model: 4C150-01) set at 190° C. and was kneaded under a nitrogen atmosphere at a rotation frequency of 50 rpm for 30 minutes. The mixture (gel) prepared by the kneading was pressed with a pressing machine heated to 165° C. to produce a gel sheet having a thickness of 1.0 mm. A test piece of 10 cm×10 cm was cut out from the produced gel sheet and was set to a simultaneous biaxial tenter stretching machine heated to 120° C. and retained for 3 minutes. The gel sheet was then stretched at a 12 mm/sec by 7.0-fold in the main direction and 7.0-fold in the transverse direction (i.e., 7×7-fold). The stretched sheet was then sufficiently immersed in normal hexane to extract and remove liquid paraffin, and the normal hexane was then dried and removed. The thin film after completion of extraction was dried at room temperature for 10 hours to obtain a microporous membrane.

(9-2) Molding of Fiber

A polymer mixture was prepared by adding 0.012 g (0.3 mass %) of pentaerythrityl-tetrakis[3-(3,5-di-t-butyl-4-hydroxyphenyl)propionate] as an oxidation inhibitor to 4.0 g of an ultra-high molecular weight ethylene-based copolymer powder and performing dry blending using a tumbler blender. The resulting polymer mixture and 36.0 g (polyethylene concentration: 10 mass %) of liquid paraffin (kinematic viscosity at 37.78° C.: $7.59 \times 10^{-5}$ m$^2$/s) were charged in a pre-mixing tank purged with nitrogen and were stirred at room temperature to obtain a uniform slurry. The slurry was supplied to a biaxial extruder with a pump under a nitrogen atmosphere and was melted and kneaded. The conditions for the melting and kneading were a preset temperature of 250° C., a screw rotation frequency of 200 rpm, and a discharge rate of 12 kg/hr. In order to impart discharge stability on the downstream side of the extruder, the melted and kneaded slurry was allowed to pass through a screen mesh composed of stacked stainless steel plain weave screens having mesh sizes of 250 μm, 106 μm, 45 μm, 106 μm, and 250 μm in accordance with JIS Z8801 via a gear pump and then a dies for spinning. The resulting strand was sufficiently immersed in normal hexane to extract and remove liquid paraffin, and the normal hexane was then dried and removed. The strand was then elongated by 20-fold at 120° C. and further by 50-fold at 140° C. to obtain fiber.

(9-3) Compression Molding (Press Molding) and Ram Molding

The ultra-high molecular weight ethylene-based copolymer powder was subjected to compression molding (press molding) or ram extrusion (under a pressure of about 12 MPa, with a horizontal ram extruder having a ram length of about 1.2 m, preset temperature: a cylinder temperature of about 240° C. and a die temperature of about 200° C.) in accordance with JIS K7139 to obtain a molded article.

(10) Evaluation of Membrane Breakage and Thread Breakage

The membrane breakage or thread breakage state during the production of the microporous membrane or the fiber was visually evaluated in the stretching processes (9-1) and (9-2). The evaluation criteria are as follows:

◯: Membrane breakage or thread breakage did not occur at all in 10 times repeated test;

Δ: Membrane breakage or thread breakage occurred once in 10 times of stretching;

X: Membrane breakage or thread breakage occurred twice or more in 10 times of stretching.

(11) Wear Resistance Test

The molded article prepared in (9-3) was subjected to a wear resistance test (sand slurry test). No. 4 silica sand was used as the sand in the test at 2 kg for 2 L of water. The wear loss rate was determined from the amount of the wear loss after a test at a rotation frequency of 1,750 rpm for 24 hours by the following mathematical expression B. A test piece of which the wear loss rate was higher than 5% was evaluated as unacceptable (×), and a test piece of which the wear loss rate was 5% or less was evaluated as satisfactory (◯).

$$\text{Wear loss rate}=(W1-W2)/W1*100 \quad \text{Mathematical expression B}$$

W1: original weight, W2: weight after the test.

(12) Evaluation of Impact Strength

A test piece having 8 cm length, 1 cm width, and 4 mm thickness was cut out from the molded article prepared in (9-3) and was evaluated for impact strength. The addition average value of measured values at 10 points was calculated as the notched Charpy impact strength. A test piece having a notched Charpy impact strength of less than 100 kJ/g was evaluated as unacceptable (×), and a test piece having a notched Charpy impact strength of 100 kJ/g or more was evaluated as satisfactory (◯).

(13) Sheet Shape in Skive Cutting

A molded article having 1 m length, 1 m width, and 0.1 m thickness prepared in (9-3) was heated to 90° C. and subjected to skive cutting so as to have a thickness of 5 mm. The resulting sheet was sandwiched between iron plates of 130° C. for 1 hour for aging and was visually evaluated by the following criteria.

◯: The sheet after aging was clearly peeled from the iron plates and did not have curving and waving on the sheet end;

Δ: The sheet after aging was difficult to be peeled off from the iron plates, but did not have curving and waving on the sheet end;

X: The sheet after aging was not clearly peeled from the iron plates, or curving and waving were not resolved even if the sheet was clearly peeled from the iron plates.

Catalyst Synthesis Example 1: Preparation of Solid Catalyst Component [A]

(1) Synthesis of Carrier (A-1)

An 8-L stainless steel autoclave sufficiently purged with nitrogen was charged with 1,000 mL of a hexane solution of 2 mol/L hydroxytrichlorosilane, and 2,550 mL (equivalent to 2.68 mol of magnesium) of a hexane solution of an organic magnesium compound represented by the compositional formula $AlMg_5(C_4H_9)_{11}(OC_4H_9)_2$ was dropwise added to the hexane solution over 4 hours with stirring at 65° C., followed by stirring at 65° C. for 1 hour to continue the reaction. After completion of the reaction, the supernatant was removed, and the residue was washed with 1,800 mL of hexane four times. The solid (carrier (A-1)) was analyzed, and the amount of magnesium contained in 1 g of the solid was 8.31 mmol.

(2) Preparation of Solid Catalyst Component [A]

To 1,970 mL of a hexane slurry containing 110 g of the carrier (A-1), 110 mL of a hexane solution of 1 mol/L titanium tetrachloride and 110 mL of a hexane solution of 1 mol/L organic magnesium compound represented by the compositional formula $AlMg_5(C_4H_9)_{11}(OSiH)_2$ were simultaneously added over 1 hour with stirring at 10° C. After the addition, the reaction was continued at 10° C. for 1 hour. After completion of the reaction, 1,100 mL of the supernatant was removed, and the residue was washed with 1,100 mL of hexane twice to prepare a solid catalyst component [A]. The amount of titanium contained in 1 g of this solid catalyst component [A] was 0.75 mmol.

Example 1: PE1

Hexane, ethylene, hydrogen, α-olefin, a catalyst, and Stadis 450 (manufactured by The Associated Octel Company) were continuously supplied to a 300-L vessel polymerization reactor equipped with a stirring device. The polymerization temperature was maintained at 75° C. by jacket cooling. The hexane was supplied at a rate of 55 L/hr. As the catalyst, a mixture of promoters, triisobutylaluminum and diisobutylaluminum hydride, and the solid catalyst component [A] were used. The solid catalyst component [A] was added to the polymerization vessel at a rate of 0.7 g/hr. The mixture of triisobutylaluminum and diisobutylaluminum hydride was added to the polymerization vessel at a rate of 9 mmol/hr. The solid catalyst component [A] and the mixture of triisobutylaluminum and diisobutylaluminum hydride were added to the polymerization reactor in equal amounts from three feeding openings at a total rate of 5 L/hr. Similarly, Stadis 450 was added to the polymerization reactor from the three feeding openings to give a concentration of 22 ppm relative to the ultra-high molecular weight ethylene-based copolymer. As the α-olefin, 1-butene was continuously added to give a concentration of 0.4 mol % relative to the ethylene gas-phase concentration. Hydrogen was continuously added to give a concentration of 0.2 mol % relative to the ethylene gas-phase concentration. The polymerization pressure was maintained at 0.4 MPa by continuously supplying ethylene. Stirring was sufficiently performed such that the inside of the polymerization reactor was uniform under these conditions. As the stirring blade in the stirring device, six turbine blades were used at a rotation frequency of 105 rpm. The production rate of the ultra-high molecular weight ethylene-based copolymer was 10 kg/hr. The catalyst activity was 30,000 g of polyethylene (PE) per 1 g of the solid catalyst component [A]. The polymer slurry was continuously supplied to a flash drum of a pressure of 0.05 MPa such that the level in the polymerization reactor was maintained constant to separate unreacted ethylene. The polymerization slurry was continuously subjected to a solvent separating step and was then sent to a drying step. The dryer was of a drum system, and the jacket was set to 80° C. under a nitrogen flow. Continuous operation was stably performed without causing aggregation of the polymer and without causing clogging of the slurry extraction pipe. Furthermore, 1,000 ppm of calcium stearate (manufactured by Dainichi Chemical Industry Co., Ltd., C60) was added to the polymer, followed by sufficient mixing with a Henschel mixer. The resulting powder was sieved with a sieve having a mesh size of 425 μm to remove powder not passed through the sieve. The thus-prepared ultra-high molecular weight ethylene-based copolymer powder is referred to as PE1.

Regarding the ultra-high molecular weight ethylene-based copolymer powder of Example 1, the molecular weight, the content of α-olefin unit, the isothermal crystallization time, the heat of fusion per unit mass (ΔH2), the content of titanium element, the bulk density, and the average particle diameter were measured according to the above-described methods. The results are shown in Table 1. In addition, the ultra-high molecular weight ethylene-based copolymer powder was molded according to the above-described method, and membrane breakage and thread breakage tests, a wear resistance test, evaluation of impact strength, and evaluation of the sheet shape in skive cutting were performed. The results are shown in Table 1.

Example 2: PE2

The same procedure as that in Example 1 was performed except that the polymerization temperature was 66° C., butene-1 as the α-olefin was continuously added to give a concentration of 0.35 mol % relative to the ethylene gas-phase concentration, and hydrogen was not supplied to obtain an ultra-high molecular weight ethylene-based copolymer powder (PE2). The resulting ultra-high molecular weight ethylene-based copolymer powder PE2 was evaluated as in Example 1. The results are shown in Table 1.

Example 3: PE3

The same procedure as that in Example 1 was performed except that the polymerization temperature was 59° C., butene-1 as the α-olefin was continuously added to give a concentration of 0.15 mol % relative to the ethylene gas-phase concentration, and hydrogen was not supplied to obtain an ultra-high molecular weight ethylene-based copolymer powder (PE3). The resulting ultra-high molecular weight ethylene-based copolymer powder PE3 was evaluated as in Example 1. The results are shown in Table 1.

Example 4: PE4

The same procedure as that in Example 1 was performed except that the polymerization temperature was 59° C., butene-1 as the α-olefin was continuously added to give a concentration of 0.95 mol % relative to the ethylene gas-phase concentration, and hydrogen was not supplied to obtain an ultra-high molecular weight ethylene-based copolymer powder (PE4). The resulting ultra-high molecular weight ethylene-based copolymer powder PE4 was evaluated as in Example 1. The results are shown in Table 1.

Example 5: PE5

The same procedure as that in Example 1 was performed except that the polymerization temperature was 93° C., butene-1 as the α-olefin was continuously added to give a concentration of 0.05 mol % relative to the ethylene gas-phase concentration, and hydrogen was added to give a concentration of 12 mol % relative to the ethylene gas-phase concentration to obtain an ultra-high molecular weight ethylene-based copolymer powder (PE5). The resulting ultra-high molecular weight ethylene-based copolymer powder PE5 was evaluated as in Example 1. The results are shown in Table 1.

Example 6: PE6

The same procedure as that in Example 1 was performed except that the polymerization temperature was 93° C., butene-1 as the α-olefin was continuously added to give a concentration of 0.83 mol % relative to the ethylene gas-phase concentration, and hydrogen was added to give a concentration of 5.5 mol % relative to the ethylene gas-phase concentration to obtain an ultra-high molecular weight ethylene-based copolymer powder (PE6). The resulting ultra-high molecular weight ethylene-based copolymer powder PE6 was evaluated as in Example 1. The results are shown in Table 1.

Example 7: PE7

The same procedure as that in Example 1 was performed except that butene-1 as the α-olefin was continuously added to give a concentration of 0.95 mol % relative to the ethylene gas-phase concentration to obtain an ultra-high molecular weight ethylene-based copolymer powder (PE7). The resulting ultra-high molecular weight ethylene-based copolymer powder PE7 was evaluated as in Example 1. The results are shown in Table 1.

Example 8: PE8

The same procedure as that in Example 2 was performed except that butene-1 as the α-olefin was continuously added to give a concentration of 0.95 mol % relative to the ethylene gas-phase concentration to obtain an ultra-high molecular weight ethylene-based copolymer powder (PE8). The resulting ultra-high molecular weight ethylene-based copolymer powder PE8 was evaluated as in Example 1. The results are shown in Table 1.

Example 9: PE9

The same procedure as that in Example 1 was performed except that the polymerization temperature was 59° C., butene-1 as the α-olefin was continuously added to give a concentration of 0.55 mol % relative to the ethylene gas-phase concentration, and hydrogen was not supplied to obtain an ultra-high molecular weight ethylene-based copolymer powder (PE9). The resulting ultra-high molecular weight ethylene-based copolymer powder PE9 was evaluated as in Example 1. The results are shown in Table 1.

Example 10: PE10

The same procedure as that in Example 1 was performed except that the polymerization pressure was 0.3 MPa to obtain an ultra-high molecular weight ethylene-based copolymer powder (PE10). The resulting ultra-high molecular weight ethylene-based copolymer powder PE10 was evaluated as in Example 1. The results are shown in Table 1.

Example 11: PE11

The same procedure as that in Example 2 was performed except that the polymerization pressure was 0.3 MPa to obtain an ultra-high molecular weight ethylene-based copolymer powder (PE11). The resulting ultra-high molecular weight ethylene-based copolymer powder PE11 was evaluated as in Example 1. The results are shown in Table 1.

Example 12: PE12

The same procedure as that in Example 1 was performed except that the polymerization temperature was 93° C., butene-1 as the α-olefin was continuously added to give a concentration of 0.05 mol % relative to the ethylene gas-phase concentration, hydrogen was added to give a concentration of 12 mol % relative to the ethylene gas-phase concentration, and the polymerization pressure was 0.25 MPa to obtain an ultra-high molecular weight ethylene-based copolymer powder (PE12). The resulting ultra-high molecular weight ethylene-based copolymer powder PE12 was evaluated as in Example 1. The results are shown in Table 1.

Example 13: PE13

The same procedure as that in Example 12 was performed except that butene-1 as the α-olefin was continuously added to give a concentration of 0.83 mol % relative to the ethylene gas-phase concentration and hydrogen was added to give a concentration of 5.5 mol % relative to the ethylene gas-phase concentration to obtain an ultra-high molecular weight ethylene-based copolymer powder (PE13). The resulting ultra-high molecular weight ethylene-based copolymer powder PE13 was evaluated as in Example 1. The results are shown in Table 1.

Example 14: PE14

The same procedure as that in Example 1 was performed except that the polymerization pressure was 0.33 MPa to obtain an ultra-high molecular weight ethylene-based copolymer powder (PE14). The resulting ultra-high molecular weight ethylene-based copolymer powder PE14 was evaluated as in Example 1. The results are shown in Table 1.

Example 15: PE15

The same procedure as that in Example 2 was performed except that the polymerization pressure was 0.33 MPa to obtain an ultra-high molecular weight ethylene-based copolymer powder (PE15). The resulting ultra-high molecular weight ethylene-based copolymer powder PE15 was evaluated as in Example 1. The results are shown in Table 1.

Example 16: PE16

The same procedure as that in Example 12 was performed except that the polymerization pressure was 0.27 MPa to obtain an ultra-high molecular weight ethylene-based copolymer powder (PE16). The resulting ultra-high molecular weight ethylene-based copolymer powder PE16 was evaluated as in Example 1. The results are shown in Table 2.

Example 17: PE17

The same procedure as that in Example 13 was performed except that the polymerization pressure was 0.27 MPa to obtain an ultra-high molecular weight ethylene-based copolymer powder (PE17). The resulting ultra-high molecular weight ethylene-based copolymer powder PE17 was evaluated as in Example 1. The results are shown in Table 2.

Example 18: PE18

The same procedure as that in Example 1 was performed except that calcium stearate was not added to obtain an ultra-high molecular weight ethylene-based copolymer powder (PE18). The resulting ultra-high molecular weight ethylene-based copolymer powder PE18 was evaluated as in Example 1. The results are shown in Table 2.

Example 19: PE19

The same procedure as that in Example 2 was performed except that calcium stearate was not added to obtain an ultra-high molecular weight ethylene-based copolymer powder (PE19). The resulting ultra-high molecular weight ethylene-based copolymer powder PE19 was evaluated as in Example 1. The results are shown in Table 2.

Example 20: PE20

The same procedure as that in Example 1 was performed except that the polymerization temperature was 82° C. and hydrogen was added to give a concentration of 0.15 mol % relative to the ethylene gas-phase concentration to obtain an ultra-high molecular weight ethylene-based copolymer powder (PE20). The resulting ultra-high molecular weight ethylene-based copolymer powder PE20 was evaluated as in Example 1. The results are shown in Table 2.

Example 21: PE21

The same procedure as that in Example 1 was performed except that the polymerization temperature was 60° C., butene-1 as the α-olefin was continuously added to give a concentration of 0.35 mol % relative to the ethylene gas-phase concentration, and hydrogen was added to give a concentration of 0.15 mol % relative to the ethylene gas-phase concentration to obtain an ultra-high molecular weight ethylene-based copolymer powder (PE21). The resulting ultra-high molecular weight ethylene-based copolymer powder PE21 was evaluated as in Example 1. The results are shown in Table 2.

Comparative Example 1: PE22

The same procedure as that in Example 1 was performed except that the polymerization temperature was 96° C., α-olefin was not added, and hydrogen was added to give a concentration of 13 mol % relative to the ethylene gas-phase concentration to obtain an ultra-high molecular weight ethylene-based copolymer powder (PE22). The resulting ultra-high molecular weight ethylene-based copolymer powder PE22 was evaluated as in Example 1. The results are shown in Table 2.

Comparative Example 2: PE23

The same procedure as that in Example 1 was performed except that the polymerization temperature was 96° C., butene-1 as the α-olefin was continuously added to give a concentration of 1.1 mol % relative to the ethylene gas-phase concentration, and hydrogen was added to give a concentration of 7.1 mol % relative to the ethylene gas-phase concentration to obtain an ultra-high molecular weight ethylene-based copolymer powder (PE23). The resulting ultra-high molecular weight ethylene-based copolymer powder PE23 was evaluated as in Example 1. The results are shown in Table 2.

Comparative Example 3: PE24

The same procedure as that in Example 1 was performed except that the polymerization temperature was 55° C. and α-olefin and hydrogen were not added to obtain an ultra-high molecular weight ethylene-based copolymer powder (PE24). The resulting ultra-high molecular weight ethylene-based copolymer powder PE24 was evaluated as in Example 1. The results are shown in Table 2.

Comparative Example 4: PE25

The same procedure as that in Example 1 was performed except that the polymerization temperature was 55° C., butene-1 as the α-olefin was continuously added to give a concentration of 1.1 mol % relative to the ethylene gas-phase concentration, and hydrogen was not supplied to obtain an ultra-high molecular weight ethylene-based copolymer powder (PE25). The resulting ultra-high molecular weight ethylene-based copolymer powder PE25 was evaluated as in Example 1. The results are shown in Table 2.

Comparative Example 5: PE26

The same procedure as that in Example 1 was performed except that the polymerization pressure was 0.2 MPa to obtain an ultra-high molecular weight ethylene-based copolymer powder (PE26). The resulting ultra-high molecular weight ethylene-based copolymer powder PE26 was evaluated as in Example 1. The results are shown in Table 2.

Comparative Example 6: PE27

The same procedure as that in Example 1 was performed except that the solid catalyst component [A] and the mixture of triisobutylaluminum and diisobutylaluminum hydride were added to the polymerization reactor from only one feeding opening and as the stirring blade in the stirring device, two turbine blades were used at a rotation frequency of 30 rpm to obtain an ultra-high molecular weight ethylene-based copolymer powder (PE27). The resulting ultra-high molecular weight ethylene-based copolymer powder PE27 was evaluated as in Example 1. The results are shown in Table 2.

Comparative Example 7: PE28

The same procedure as that in Comparative Example 6 was performed except that the polymerization temperature was 71° C., butene-1 as the α-olefin was continuously added to give a concentration of 0.50 mol % relative to the ethylene gas-phase concentration, Stadis 450 was added to give a concentration of 10 ppm relative to the ultra-high molecular weight ethylene-based copolymer, calcium stearate was not added, and in microporous membrane molding, fiber molding, compression molding (press molding), or ram molding of the resulting ultra-high molecular weight ethylene-based copolymer powder, 500 ppm of 2,5-dimethyl-2,5-bis(t-butylperoxy)hexane (trade name: "Perhexa 25B", manufactured by NOF Corporation) was added and blended as an organic peroxide (crosslinking agent) to obtain an ultra-high molecular weight ethylene-based copolymer powder (PE28). The resulting ultra-high molecular weight ethylene-based copolymer powder PE28 was evaluated as in Example 1. The results are shown in Table 2.

Comparative Example 8: PE29

The same procedure as that in Example 1 was performed except that the polymerization temperature was 82° C. to obtain an ultra-high molecular weight ethylene-based copolymer powder (PE29). The resulting ultra-high molecular weight ethylene-based copolymer powder PE29 was evaluated as in Example 1. The results are shown in Table 2.

TABLE 1

|  | Example 1 | Example 2 | Example 3 | Example 4 | Example 5 | Example 6 | Example 7 |
|---|---|---|---|---|---|---|---|
| Polymerization temperature (° C.) | 75 | 66 | 59 | 59 | 93 | 93 | 75 |
| Polymerization pressure (MPa) | 0.4 | 0.4 | 0.4 | 0.4 | 0.4 | 0.4 | 0.4 |
| α-Olefin | Butene-1 | Butene-1 | Butene-1 | Butene-1 | Butene-1 | Butene-1 | Butene-1 |
| Gas-phase α-olefin concentration (mol %) | 0.4 | 0.35 | 0.15 | 0.95 | 0.05 | 0.83 | 0.95 |
| Gas-phase hydrogen concentration (mol %) | 0.2 | 0 | 0 | 0 | 12 | 5.5 | 0.2 |
| Amount of Stadis 450 (ppm) | 22 | 22 | 22 | 22 | 22 | 22 | 22 |
| Amount of calcium stearate (ppm) | 1,000 | 1,000 | 1,000 | 1,000 | 1,000 | 1,000 | 1,000 |
| Viscosity-average molecular weight (Mv) ($\times 10^4$) | 300 | 650 | 985 | 970 | 15 | 18 | 300 |
| Content of α-olefin unit (mol %) | 0.04 | 0.025 | 0.012 | 0.096 | 0.013 | 0.095 | 0.092 |
| Isothermal crystallization time (min) | 10.9 | 9.1 | 5.2 | 13.1 | 10.5 | 17.2 | 13.5 |
| Heat of fusion per unit mass (ΔH2) | 148.8 | 144 | 149.1 | 140.1 | 196.6 | 175.5 | 145.9 |
| Titanium element content (ppm) | 1 | 2.5 | 3.4 | 1.5 | 1.5 | 1.6 | 2.9 |
| Bulk density (g/cm$^3$) | 0.50 | 0.46 | 0.47 | 0.49 | 0.48 | 0.43 | 0.47 |
| Tap density (g/cm$^3$) | 0.59 | 0.57 | 0.55 | 0.54 | 0.56 | 0.55 | 0.54 |
| Ratio of tap density to bulk density | 1.18 | 1.24 | 1.17 | 1.10 | 1.17 | 1.28 | 1.15 |
| Average particle diameter (μm) | 89.8 | 78.1 | 102.4 | 103.5 | 65.4 | 72.9 | 105.7 |
| Evaluation decision of membrane breakage in molding of microporous membrane | ○ | ○ | ○ | ○ | ○ | ○ | ○ |
| Evaluation decision of thread breakage in molding | ○ | ○ | ○ | ○ | ○ | ○ | ○ |

TABLE 1-continued

|  |  | | | | | | | |
|---|---|---|---|---|---|---|---|---|
| of fiber | | | | | | | | |
| Wear resistance test of press molded product (wear loss) | % | 2.5 | 1.5 | 1.0 | 0.9 | 3.4 | 3.7 | 2.6 |
| | Decision | ○ | ○ | ○ | ○ | ○ | ○ | ○ |
| Impact strength of press molded product | kJ/g | 140 | 146 | 118 | 167 | 105 | 153 | 154 |
| | Decision | ○ | ○ | ○ | ○ | ○ | ○ | ○ |
| Sheet shape in skive cutting of press molded product | | ○ | ○ | ○ | ○ | ○ | ○ | ○ |
| Wear resistance test of ram extrusion product (wear loss) | % | 2.5 | 1.6 | — | — | — | — | — |
| | Decision | ○ | ○ | — | — | — | — | — |
| Impact strength of ram extrusion product | kJ/g | 139 | 144 | — | — | — | — | — |
| | Decision | ○ | ○ | — | — | — | — | — |
| Sheet shape in skive cutting of ram extrusion product | | ○ | ○ | — | — | — | — | — |

|  | Example 8 | Example 9 | Example 10 | Example 11 | Example 12 | Example 13 | Example 14 | Example 15 |
|---|---|---|---|---|---|---|---|---|
| Polymerization temperature (° C.) | 66 | 59 | 75 | 66 | 93 | 93 | 75 | 66 |
| Polymerization pressure (MPa) | 0.4 | 0.4 | 0.3 | 0.3 | 0.25 | 0.25 | 0.33 | 0.33 |
| α-Olefin | Butene-1 | Butene-1 | Butene-1 | Butene-1 | Butene-1 | Butene-1 | Butene-1 | Butene-1 |
| Gas-phase α-olefin concentration (mol %) | 0.95 | 0.55 | 0.4 | 0.35 | 0.05 | 0.83 | 0.4 | 0.35 |
| Gas-phase hydrogen concentration (mol %) | 0 | 0 | 0.2 | 0 | 12 | 5.5 | 0.2 | 0 |
| Amount of Stadis 450 (ppm) | 22 | 22 | 22 | 22 | 22 | 22 | 22 | 22 |
| Amount of calcium stearate (ppm) | 1,000 | 1,000 | 1,000 | 1,000 | 1,000 | 1,000 | 1,000 | 1,000 |
| Viscosity-average molecular weight (Mv) (×$10^4$) | 600 | 950 | 320 | 655 | 12 | 16 | 315 | 650 |
| Content of α-olefin unit (mol %) | 0.09 | 0.05 | 0.03 | 0.03 | 0.011 | 0.094 | 0.04 | 0.03 |
| Isothermal crystallization time (min) | 12.8 | 10.4 | 6.2 | 5.7 | 5.3 | 7.1 | 6.8 | 6.2 |
| Heat of fusion per unit mass (ΔH2) | 142.7 | 143.8 | 158.2 | 154.9 | 198.9 | 173.4 | 155.5 | 153.9 |
| Titanium element content (ppm) | 3.2 | 2.5 | 6.8 | 6.9 | 6.4 | 6.3 | 5.7 | 5.8 |
| Bulk density (g/cm$^3$) | 0.43 | 0.43 | 0.44 | 0.46 | 0.44 | 0.46 | 0.48 | 0.46 |
| Tap density (g/cm$^3$) | 0.54 | 0.55 | 0.62 | 0.55 | 0.53 | 0.55 | 0.57 | 0.57 |
| Ratio of tap density to bulk density | 1.26 | 1.28 | 1.41 | 1.20 | 1.20 | 1.20 | 1.41 | 1.24 |
| Average particle diameter (μm) | 104.6 | 103.8 | 91.5 | 88.6 | 71.1 | 74.4 | 90.9 | 83.0 |
| Evaluation decision of membrane breakage in molding of microporous membrane | ○ | ○ | ○ | ○ | ○ | ○ | ○ | ○ |
| Evaluation decision of thread breakage in molding of fiber | ○ | ○ | Δ | Δ | Δ | Δ | ○ | ○ |
| Wear resistance test of press molded product (wear loss) % | 1.3 | 1.4 | 3.2 | 2.1 | 4.7 | 4.8 | 3.0 | 1.9 |
| Decision | ○ | ○ | ○ | ○ | ○ | ○ | ○ | ○ |
| Impact strength of press molded product kJ/g | 158 | 146 | 125 | 132 | 110 | 160 | 130 | 131 |
| Decision | ○ | ○ | ○ | ○ | ○ | ○ | ○ | ○ |
| Sheet shape in skive cutting of press molded product | ○ | ○ | Δ | Δ | Δ | Δ | ○ | ○ |
| Wear resistance test of ram extrusion product (wear loss) % | — | — | — | — | — | — | — | — |
| Decision | — | — | — | — | — | — | — | — |
| Impact strength of ram extrusion product kJ/g | — | — | — | — | — | — | — | — |
| Decision | — | — | — | — | — | — | — | — |
| Sheet shape in skive cutting of ram extrusion product | — | — | — | — | — | — | — | — |

TABLE 2

|  | Example 16 | Example 17 | Example 18 | Example 19 | Example 20 | Example 21 | Comparative Example 1 | Comparative Example 2 |
|---|---|---|---|---|---|---|---|---|
| Polymerization temperature (° C.) | 93 | 93 | 75 | 66 | 82 | 60 | 96 | 96 |
| Polymerization pressure (MPa) | 0.27 | 0.27 | 0.4 | 0.4 | 0.4 | 0.4 | 0.4 | 0.4 |
| α-Olefin | Butene-1 | Butene-1 | Butene-1 | Butene-1 | Butene-1 | Butene-1 | Butene-1 | Butene-1 |
| Gas-phase α-olefin concentration (mol %) | 0.05 | 0.83 | 0.4 | 0.35 | 0.4 | 0.35 | 0 | 1.1 |
| Gas-phase hydrogen concentration (mol %) | 12 | 5.5 | 0.2 | 0 | 0.15 | 0.15 | 13 | 7.1 |
| Amount of Stadis 450 (ppm) | 22 | 22 | 22 | 22 | 22 | 22 | 22 | 22 |
| Amount of calcium stearate (ppm) | 1,000 | 1,000 | 0 | 0 | 1,000 | 1,000 | 1,000 | 1,000 |
| Viscosity-average molecular weight (Mv) (×$10^4$) | 13 | 15 | 310 | 650 | 315 | 635 | 9.3 | 9.5 |
| Content of α-olefin unit (mol %) | 0.012 | 0.095 | 0.03 | 0.03 | 0.03 | 0.03 | 0 | 0.11 |
| Isothermal crystallization time (min) | 5.9 | 7.4 | 10.4 | 9.2 | 10.6 | 9.5 | 11.2 | 18.9 |
| heat of fusion per unit mass (ΔH2) | 199.1 | 174.4 | 146.9 | 142.7 | 145.3 | 147.4 | 202.1 | 176.3 |
| Titanium element content (ppm) | 5.6 | 5.5 | 1.2 | 2.2 | 3.5 | 5.5 | 1.4 | 2.4 |
| Bulk density (g/cm$^3$) | 0.45 | 0.48 | 0.41 | 0.41 | 0.37 | 0.34 | 0.46 | 0.43 |
| Tap density (g/cm$^3$) | 0.54 | 0.56 | 0.60 | 0.59 | 0.58 | 0.56 | 0.59 | 0.55 |
| Ratio of tap density to bulk | 1.20 | 1.17 | 1.46 | 1.44 | 1.57 | 1.65 | 1.28 | 1.28 |

TABLE 2-continued

|  |  |  |  |  |  |  |  |  |
|---|---|---|---|---|---|---|---|---|
| density |  |  |  |  |  |  |  |  |
| Average particle diameter (μm) |  | 73.5 | 73.5 | 85.2 | 77.4 | 93.2 | 102.5 | 73.1 | 74.3 |
| Evaluation decision of membrane breakage in molding of microporous membrane |  | ○ | ○ | ○ | ○ | Δ | Δ | X | X |
| Evaluation decision of thread breakage in molding of fiber |  | ○ | ○ | ○ | ○ | Δ | Δ | X | X |
| Wear resistance test | % | 4.3 | 4.3 | 2.7 | 1.6 | 4.3 | 2.3 | 5.3 | 5.6 |
| of press molded product (wear loss) | Decision | ○ | ○ | ○ | ○ | ○ | ○ | X | X |
| Impact strength of | kJ/g | 112 | 162 | 139 | 144 | 102 | 104 | 75 | 77 |
| press molded product | Decision | ○ | ○ | ○ | ○ | ○ | ○ | X | X |
| Sheet shape in skive cutting of press molded product |  | ○ | ○ | Δ | Δ | Δ | Δ | X | ○ |

|  | Comparative Example 3 | Comparative Example 4 | Comparative Example 5 | Comparative Example 6 | Comparative Example 7 | Comparative Example 8 |
|---|---|---|---|---|---|---|
| Polymerization temperature (° C.) | 55 | 55 | 75 | 75 | 71 | 82 |
| Polymerization pressure (MPa) | 0.4 | 0.4 | 0.2 | 0.4 | 0.4 | 0.4 |
| α-Olefin | Butene-1 | Butene-1 | Butene-1 | Butene-1 | Butene-1 | Butene-1 |
| Gas-phase α-olefin concentration (mol %) | 0 | 1.1 | 0.4 | 0.4 | 0.5 | 0.4 |
| Gas-phase hydrogen concentration (mol %) | 0 | 0 | 0.2 | 0.2 | 0.2 | 5.5 |
| Amount of Stadis 450 (ppm) | 22 | 22 | 22 | 22 | 10 | 22 |
| Amount of calcium stearate (ppm) | 1,000 | 1,000 | 1,000 | 1,000 | 0 | 1,000 |
| Viscosity-average molecular weight (Mv) (×10$^4$) | 1,100 | 1,100 | 300 | 320 | 350 | 85 |
| Content of α-olefin unit (mol %) | 0 | 0.11 | 0.03 | 0.03 | 0.04 | 0.03 |
| Isothermal crystallization time (min) | 3.4 | 19.1 | 4.3 | 4.2 | 4.2 | 3.2 |
| heat of fusion per unit mass (ΔH2) | 158.2 | 140.5 | 163.5 | 156.1 | 155.2 | 160.2 |
| Titanium element content (ppm) | 3.2 | 3.4 | 15 | 1.3 | 1.3 | 1.8 |
| Bulk density (g/cm$^3$) | 0.45 | 0.46 | 0.42 | 0.57 | 0.46 | 0.45 |
| Tap density (g/cm$^3$) | 0.55 | 0.53 | 0.54 | 0.59 | 0.47 | 0.59 |
| Ratio of tap density to bulk density | 1.22 | 1.15 | 1.29 | 1.04 | 1.02 | 1.31 |
| Average particle diameter (μm) | 103.9 | 108.5 | 90.9 | 116.2 | 112.5 | 72.5 |
| Evaluation decision of membrane breakage in molding of microporous membrane | X | X | ○ | ○ | ○ | ○ |
| Evaluation decision of thread breakage in molding of fiber | X | X | ○ | ○ | ○ | ○ |
| Wear resistance test % | 1.9 | 1.5 | 2.7 | 4.2 | 2.5 | 5.3 |
| of press molded product (wear loss) Decision | ○ | ○ | ○ | ○ | ○ | X |
| Impact strength of kJ/g | 84 | 85 | 98 | 107 | 140 | 76 |
| press molded product Decision | X | X | X | X | ○ | X |
| Sheet shape in skive cutting of press molded product | X | ○ | X | X | X | X |

From the above, it is demonstrated that the ultra-high molecular weight ethylene-based copolymer powder of the present invention is excellent in that it is not only capable of achieving a balance between wear resistance and shock resistance after molding but also capable of suppressing the curving of a molded sheet and that the molded sheet can be easily peeled from the mold used for aging thereof and also in a separator for a secondary battery or fiber, membrane breakage or thread breakage due to foreign substances can be suppressed.

In addition, these molded articles prepared using the ultra-high molecular weight ethylene-based copolymer powder have excellent physical properties described above and therefore can be suitably used in, for example, separators for secondary batteries, such as a lithium ion secondary battery and a lead storage battery; fiber; lining materials for, for example, hoppers and chutes, having non-tackiness and low coefficients of friction; and bearings, gears, roller guide rails, bone substitutes, bone conductive materials, and osteoinduction materials, which are required to be self-lubricating, have a low coefficient of friction, and be wear resistant.

INDUSTRIAL APPLICABILITY

The ultra-high molecular weight ethylene-based copolymer powder of the present invention is excellent in that not only a balance between wear resistance and shock resistance after molding can be achieved, but also the sheet curved in cutting the molded article to a skive shape can be easily peeled from the mold after aging and also is excellent in that a separator for a secondary battery or fiber can be suppressed from membrane breakage or thread breakage due to foreign substances, and accordingly has industrial applicability in a wide range of applications, such as application to molding.

The invention claimed is:
1. An ultra-high molecular weight ethylene-based copolymer powder comprising:
an ethylene unit and an α-olefin unit having 3 or more and 8 or less carbon atoms as structural units, wherein the ultra-high molecular weight ethylene-based copolymer powder has a viscosity-average molecular weight of 100,000 or more and 10,000,000 or less, a content of the α-olefin unit is 0.01 mol % or more and 0.10 mol % or less based on a total amount of the ethylene unit and the α-olefin unit, and in measurement with a differential scanning calorimeter under following conditions, an isothermal crystallization time is determined as a time from reaching 126° C. of Step A3 as a starting point (0 min) to giving an exothermic peak top due to crystallization and the isothermal crystallization time is 5 minutes or more (Conditions for measurement of isothermal crystallization time);

Step A1: holding at 50° C. for 1 minute and then an increase up to 180° C. at a temperature rise rate of 10° C./min, Step A2: holding at 180° C. for 30 minutes and then a decrease down to 126° C. at a temperature drop rate of 80° C./min, and Step A3: holding at 126° C.

2. The ultra-high molecular weight ethylene-based copolymer powder according to claim 1, wherein in measurement with a differential scanning calorimeter under following conditions, a heat of fusion per unit mass (ΔH2) in a temperature rising process of Step B3 is 230 J/g or less (Conditions for measuring heat of fusion per unit mass (ΔH2));

Step B1: holding at 50° C. for 1 minute and then an increase up to 180° C. at a temperature rise rate of 10° C./min, Step B2: holding at 180° C. for 5 minutes and then a decrease down to 50° C. at a temperature drop rate of 10° C./min, and Step B3: holding at 50° C. for 5 minutes and then an increase up to 180° C. at a temperature rise rate of 10° C./min.

3. The ultra-high molecular weight ethylene-based copolymer powder according to claim 1, wherein a content of titanium element measured with an inductively coupled plasma mass spectrometer (ICP/MS) is 6 ppm or less.

4. The ultra-high molecular weight ethylene-based copolymer powder according to claim 1, wherein the isothermal crystallization time is 8 minutes or more.

5. The ultra-high molecular weight ethylene-based copolymer powder according to claim 1, wherein the ultra-high molecular weight ethylene-based copolymer powder has a tap density of 0.51 g/cm$^3$ or more and 0.64 g/cm$^3$ or less, and a bulk density of 0.40 g/cm$^3$ or more and 0.60 g/cm$^3$ or less.

6. The ultra-high molecular weight ethylene-based copolymer powder according to claim 5, wherein a ratio of the tap density to the bulk density is 1.10 or more and 1.50 or less.

7. The ultra-high molecular weight ethylene-based copolymer powder according to claim 1, wherein the ultra-high molecular weight ethylene-based copolymer powder has an average particle diameter of 50 μm or more and 200 μm or less.

8. A molded article of the ultra-high molecular weight ethylene-based copolymer powder according to claim 1.

9. The molded article according to claim 8, wherein the molded article is a separator membrane for a secondary battery or fiber prepared by wet extrusion.

10. The molded article according to claim 9, wherein the secondary battery is a lithium ion secondary battery or a lead storage battery.

11. The molded article according to claim 9, wherein a product using the fiber is rope, net, bulletproof clothing, a protective garment, protective gloves, a fiber reinforced concrete product, or a helmet.

12. The molded article according to claim 8, wherein the molded article is used in a lining application, a bearing, a gear, a roller guide rail, a bone substitute, a bone conductive material, or an osteoinduction material.

* * * * *